(12) United States Patent
Ryan et al.

(10) Patent No.: US 7,004,940 B2
(45) Date of Patent: Feb. 28, 2006

(54) DEVICES FOR PERFORMING THERMAL ABLATION HAVING MOVABLE ULTRASOUND TRANSDUCERS

(75) Inventors: Thomas P. Ryan, Flemington, NJ (US); Gennady Kleyman, Brooklyn, NY (US)

(73) Assignee: Ethicon, Inc., Somerville, NJ (US)

( * ) Notice: Subject to any disclaimer, the term of this patent is extended or adjusted under 35 U.S.C. 154(b) by 121 days.

(21) Appl. No.: 10/268,448

(22) Filed: Oct. 10, 2002

(65) Prior Publication Data

US 2004/0073204 A1    Apr. 15, 2004

(51) Int. Cl.
*A61B 18/18* (2006.01)

(52) U.S. Cl. .................. 606/41; 601/2; 601/3; 600/437

(58) Field of Classification Search ............... 601/2, 601/3; 600/437, 439, 459, 462, 466, 467; 606/41–50
See application file for complete search history.

(56) References Cited

U.S. PATENT DOCUMENTS

| | | |
|---|---|---|
| 5,437,629 A | 8/1995 | Goldrath |
| 5,620,479 A | 4/1997 | Diederich |
| 5,733,315 A | 3/1998 | Burdette et al. |
| 5,769,880 A | 6/1998 | Truckai et al. |
| 5,853,368 A | 12/1998 | Solomon et al. |
| 6,066,139 A | 5/2000 | Ryan et al. |
| 6,451,016 B1 * | 9/2002 | Karakozian ............... 606/41 |
| 6,595,989 B1 * | 7/2003 | Schaer .................... 606/41 |
| 6,645,202 B1 | 11/2003 | Pless et al. |

OTHER PUBLICATIONS

Neuwirth, et al, "The Endometrial Ablator: A New Instrument", Obst. & Gyn., 1994, vol. 83, No. 5, Part 1, 792-796.
Prior, et al., "Treatment of Mennorrhagia By Radiofrequency Heating", Int. J. Hyperthermia, 1991 vol. 7, No. 2, 213-220.

* cited by examiner

*Primary Examiner*—Rosiland Rollins

(57) ABSTRACT

A device for thermal ablation therapy having a handle sized and shaped to be held by a user, one or more transducer assembly which, when activated, emits ultrasound energy capable of heating tissue and which is movably mounted relative to said handle element, and moving means, such as one or more rods, for moving the transducer assembly or assemblies, while activated, to any one of a plurality of positions relative to the handle element and relative to tissue to be ablated, whereby ultrasound energy is efficiently delivered to the tissue. The device also includes carrying means, such as a shaft attached at one end to the handle element, which carries the rod or rods and the transducer assembly or assemblies. The rod or rods are engaged with a knob positioned in the handle and when the knob is rotated, the rod or rods are rotated, thereby causing the transducer assembly or assemblies to move relative to the handle, the shaft and the tissue to be ablated.

16 Claims, 10 Drawing Sheets

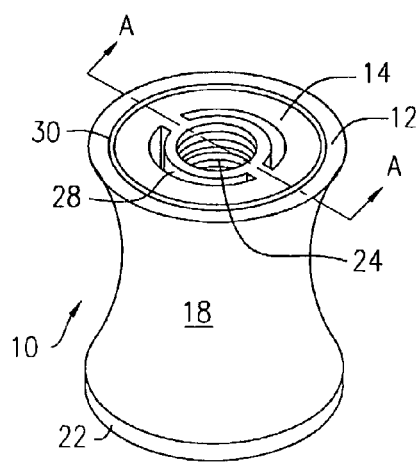
FIG. 1A
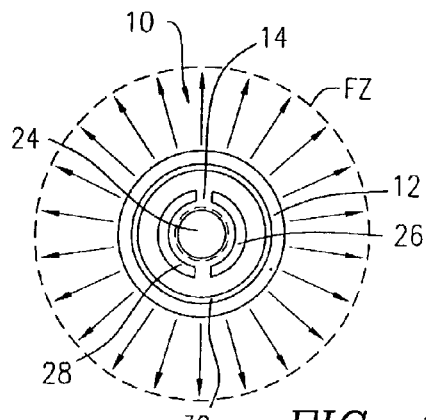
FIG. 1C
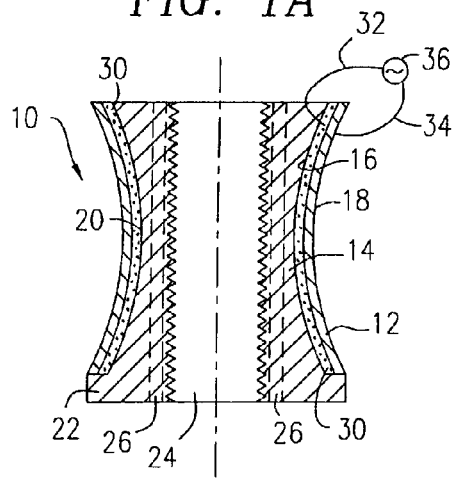
FIG. 1B
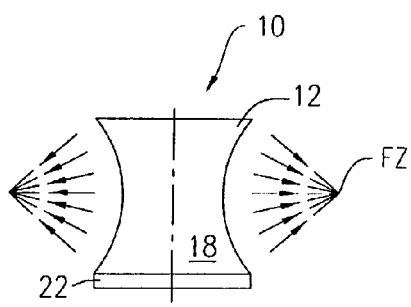
FIG. 1D
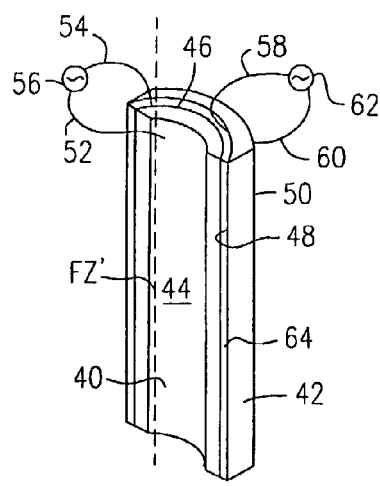
FIG. 2A
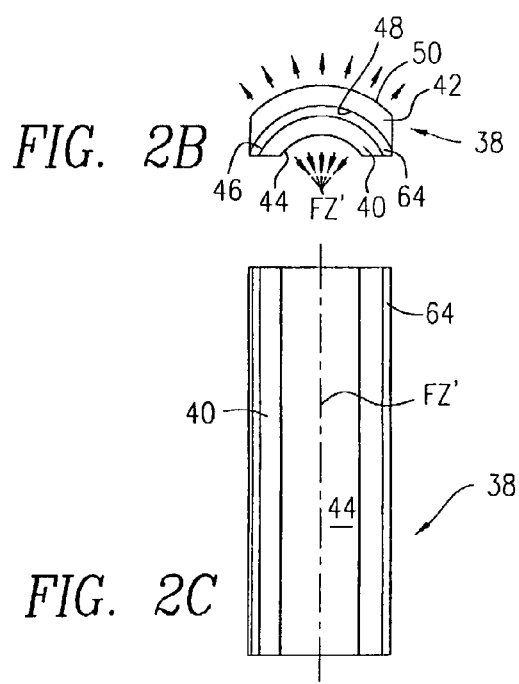
FIG. 2B
FIG. 2C

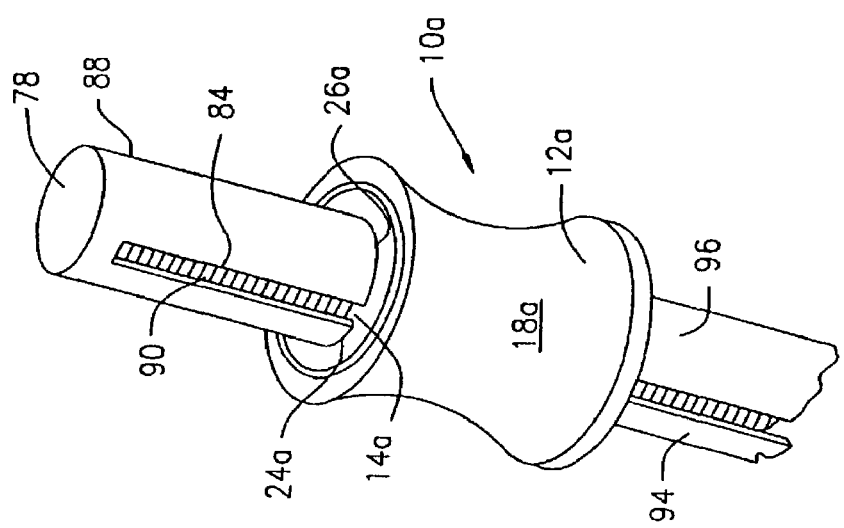
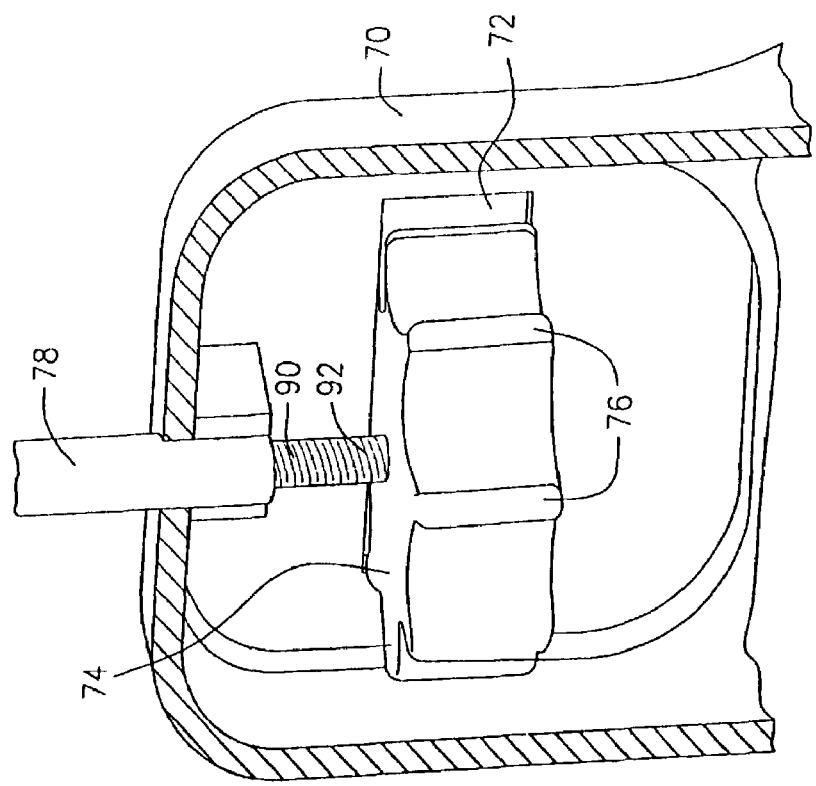
FIG. 9
FIG. 8

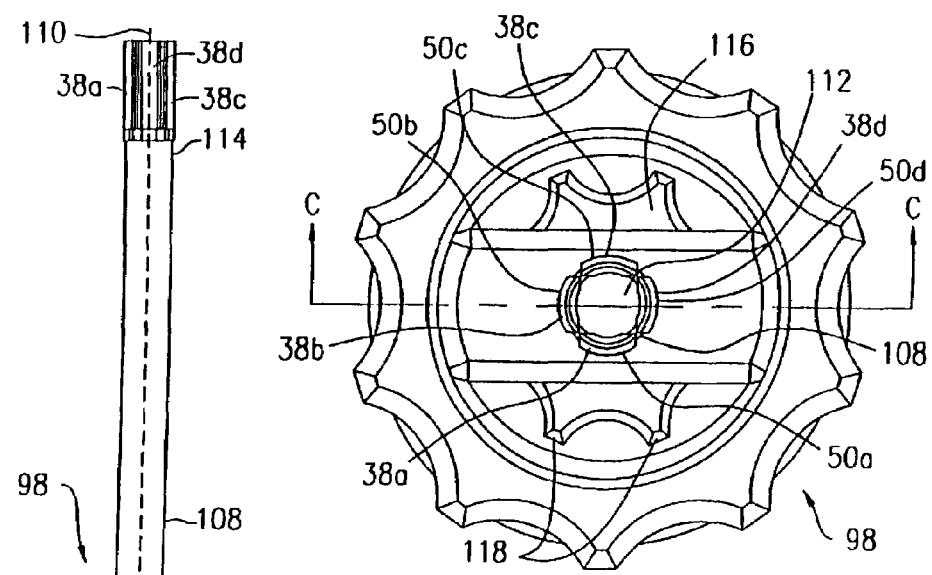
FIG. 13
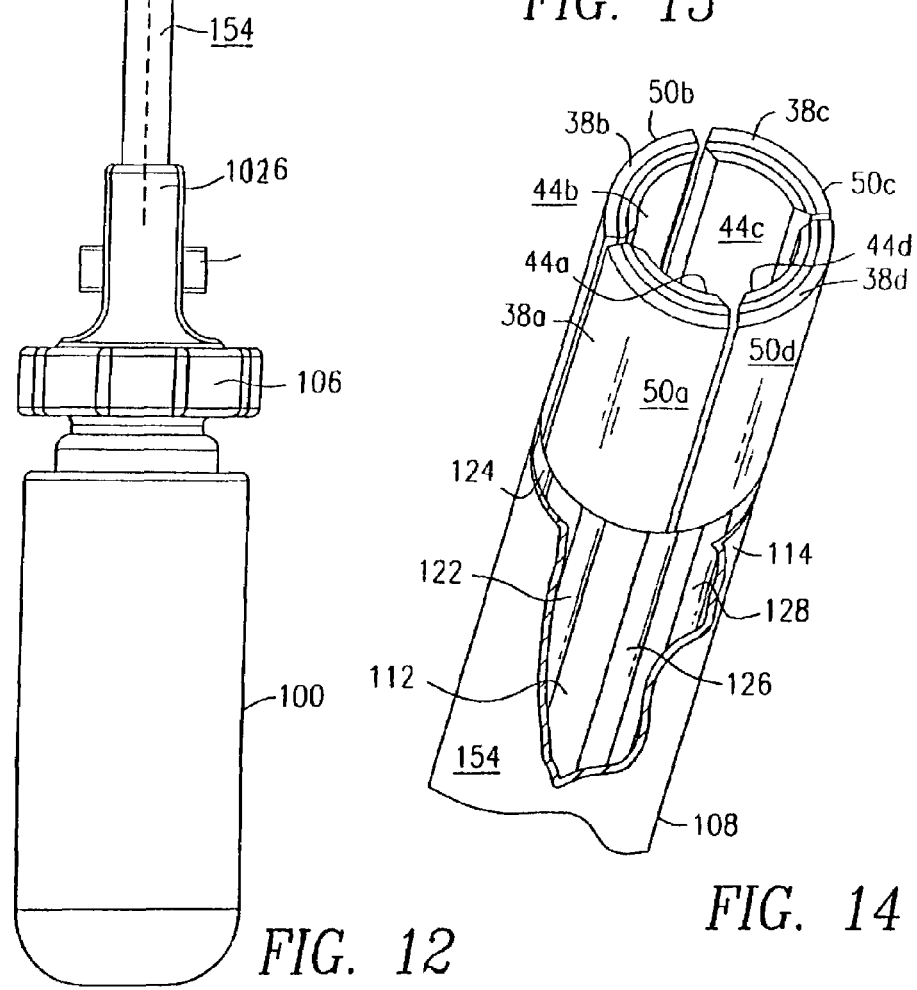
FIG. 12
FIG. 14

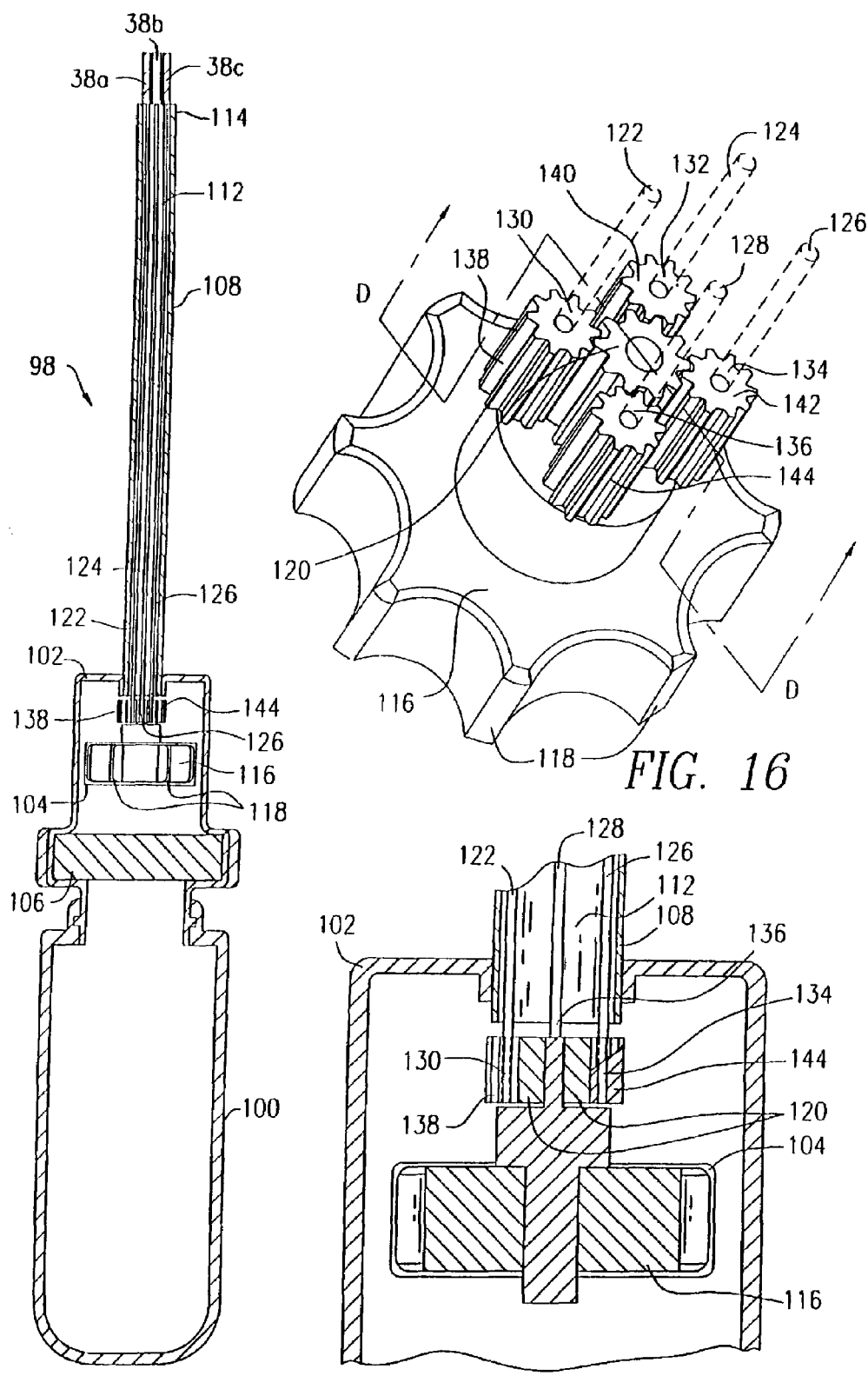

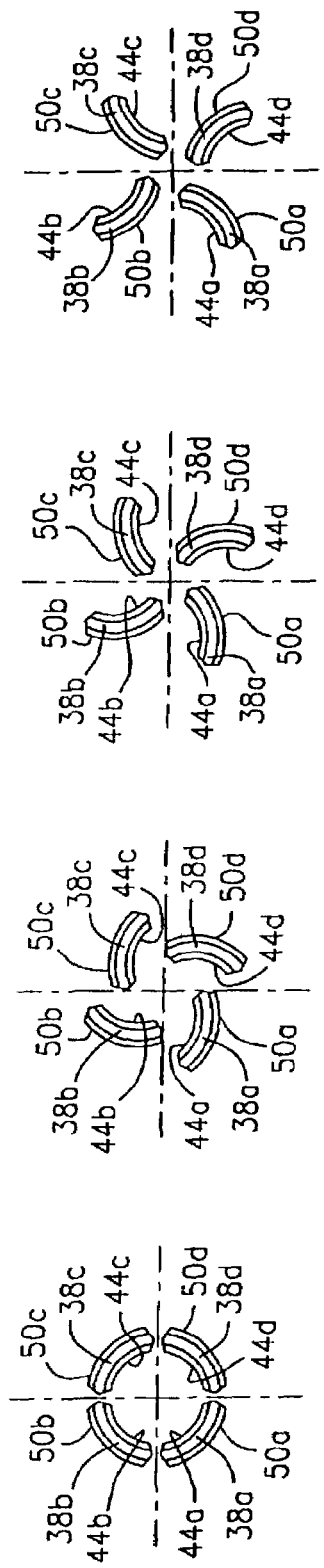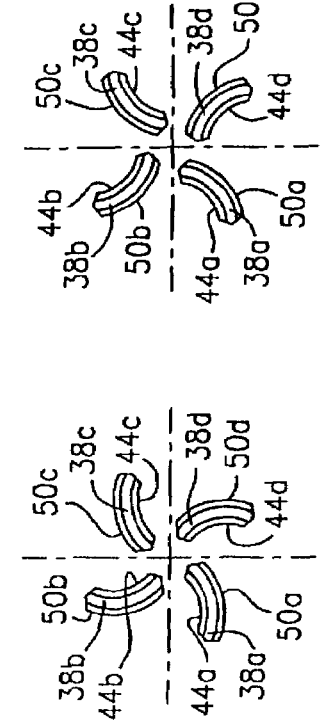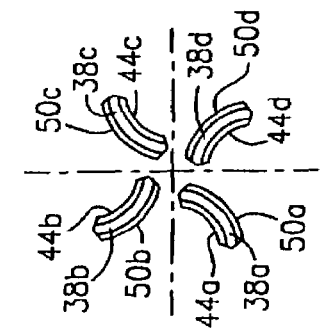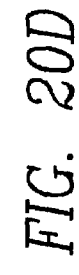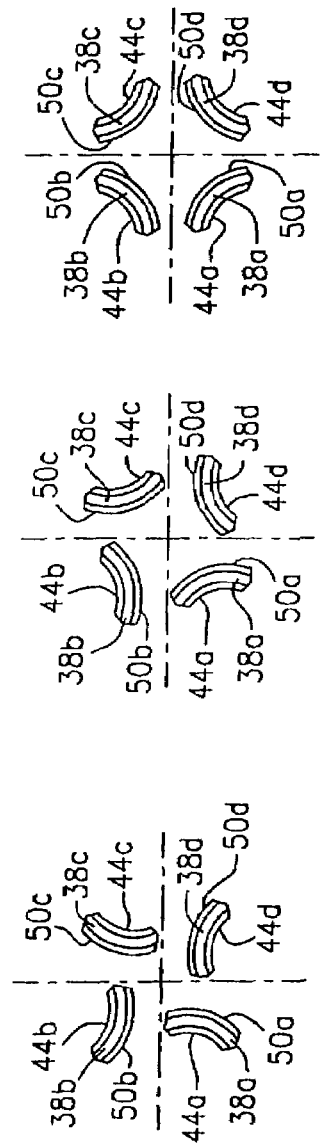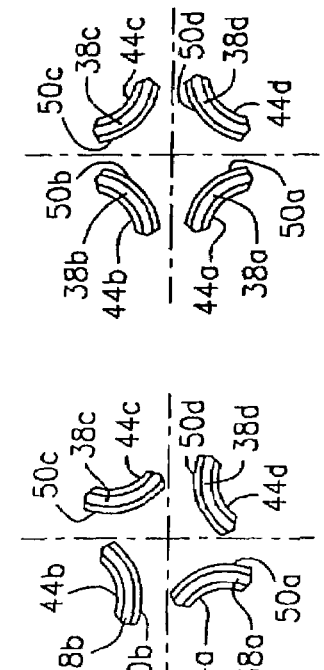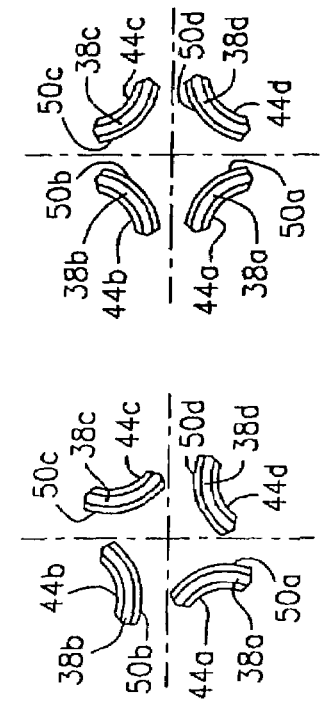

DEVICES FOR PERFORMING THERMAL ABLATION HAVING MOVABLE ULTRASOUND TRANSDUCERS

FIELD OF THE INVENTION

The present invention relates to devices for performing thermal ablation that have one or more ultrasound transducers that are movable, while activated, to efficiently deliver ultrasound energy to bodily tissue.

BACKGROUND OF THE INVENTION

There are many illnesses and medical conditions for which thermal ablation is an appropriate and effective treatment. Such conditions include, but are not limited to, prostate disorders including cancer, uterine dysfunction such as menorrhagia, rectal polyps, rectal and colon cancers, throat and oral cancers, various types of tumors, esophageal disorders such as Barrett's esophagus, etc.

Thermal ablation is a general term that is used to describe the technique of heating tissue that is diseased, or otherwise in need of treatment, in order to destroy tissue, at least down to a certain depth, thereby eliminating the disease or disorder, or at least reducing the symptoms thereof. There are many devices on the market and in clinical trials which utilize different types of energy, including radiofrequency (RF) energy, microwave energy, and ultrasound energy, to perform thermal ablation. The goal for each of these devices is, of course, the same—tissue destruction by thermal coagulation.

For example, Neuwirth, et al, "The Endometrial Ablator: A New Instrument", Obst. & Gyn., 1994, Vol. 83, No. 5, Part 1, 792–796, performed endometrial ablation using a dextrose-filled balloon device mounted at the end of a carrier catheter and including a heating element inside the balloon. The heating element is a resistive heating coil that is used to heat the fluid within the balloon, which in turn, heats the endometrial tissue that is in contact with the exterior balloon surface. Neuwirth, et al. determined that if the surface of the balloon-tissue interface is maintained at about 90° C. for 7–12 minutes, the depth of damage to the endometrium was about 4–10 millimeters.

High frequency, or radiofrequency (RF), energy has been used to perform thermal ablation of endometrial tissue. For example, Prior, et al., "Treatment of Mennorrhagia By Radiofrequency Heating", Int. J. Hyperthermia, 1991 Vol. 7, No. 2, 213–220, achieved a significant reduction in dysfunctional uterine bleeding using a device that includes a probe having a high frequency RF energy source that is inserted directly into the patient's uterus through the vagina and cervix. This energy source is an RF system having an electrode on the probe and a belt placed around the patient that serves as the return electrode. This RF system is operated at 27.12 MHz at a power of 550 Watts for about 20 minutes and achieves a deeper penetration than the Neuwirth, et al. device, which is an advantage over the Neuwirth, et al. device. However, this system suffers from the drawback that the location of the return electrode results in a scattering of the RF energy and less efficient delivery of the RF energy to the specific tissue to be treated.

U.S. Pat. No. 6,066,139 discloses a device that utilizes RF energy to perform transcervical sterilization by thermal ablation, as well as embolotherapy wherein the blood supply to tumors is reduced by sealing arterial feeder vessels. This device has two or more RF bipolar electrodes attached to the distal end of a catheter for delivery of RF energy for creating thermal lesions within the fallopian tubes that occlude the fallopian tube opening over time. While this device is generally successful at enabling the surgeon to manipulate the field of treatment, without the necessity of moving the catheter during the procedure, by selecting which combinations of electrodes are activated, there are still some limitations deriving from the unavoidable scattering of some of the RF energy and due to the fact that the RF energy travels only between the electrodes, which are located in fixed positions. Thus, this device fails to enable the surgeon to truly focus and refocus the energy emitted from the device on specific tissue areas during the surgical procedure. U.S. Pat. No. 6,066,139 also discloses an alternative embodiment wherein the RF electrodes are replaced with piezoelectric transducers and the device, therefore, emits ultrasound energy rather than RF energy.

A system marketed under the tradename THERMA-CHOICE®, by Ethicon, Inc. of Somerville, N.J., is currently used to perform thermal ablation of endometrial tissue. This system includes a latex balloon into which is circulated a heated dextrose and water solution. The balloon is attached to the distal end of a catheter carrier, through which the heated solution is circulated into the balloon, and the device often delivers satisfactory results. Some patients, however, present a need for deeper and broader endometrial penetration during ablation. In addition, it is noted that this device is particularly suited to thermal ablation of a relatively unfocused, broad tissue area, such as the inner tissue lining of a cavity or luminal structure and would not be suitable for focusing energy upon specific tissue areas.

U.S. Pat. No. 5,620,479 discloses a device for thermal treatment using ultrasound energy and having an array of tubular piezoelectric transducers disposed on a semi-flexible tubular carrier for delivering ultrasound energy directly to tissue to be ablated. The transducers are covered with a sealant coating and there is an outer covering over the sealant coating. U.S. Pat. No. 5,733,315 also discloses a device for ablating tissue using ultrasound energy that is adapted specifically for insertion into the rectum for treating the prostate. This device includes one or more ultrasound transducers disposed at least partly about a support tube, each ultrasound transducer having inactivated portions for reducing ultrasound energy directed to the rectal wall. The transducers of this device are also enclosed in a sealant.

U.S. Pat. No. 5,437,629 discloses an apparatus and method for recirculating heated fluid in the uterus to perform endometrial ablation, without using a balloon. U.S. Pat. No. 5,769,880 discloses an apparatus and method for performing thermal ablation, including endometrial tissue ablation, using bipolar RF energy. This device includes an electrode-carrying member mounted to the distal end of a shaft and an array of electrodes mounted to the surface of the electrode carrying member. A vacuum is utilized to draw out vapors, which are created when the tissue is ablated.

The foregoing devices and techniques all deliver energy in a general manner, without the ability to control or direct the application of energy in situ to the tissue to be treated. Lastly, the aforesaid devices are not designed to be movable during the time for which the energy source is activated, such that the emitted energy is redirected to particular tissue, thereby enabling a continuous treatment procedure.

The device of the present invention addresses the shortcomings of the existing apparatus and process for thermal ablation (especially endometrial ablation) by providing a device that delivers ultrasound energy to tissue to be treated in a controlled, focused and efficient manner. More particularly, the device has piezoelectric transducers that are mounted on one or more carriers such that transducers are movable, in situ during the treatment procedure, after initial positioning of the device and while the transducers are activated.

SUMMARY OF THE INVENTION

A device for thermal ablation therapy having a handle sized and shaped to be held by a user, one or more transducer assemblies which, when activated, emit ultrasound energy capable of heating tissue and which is movably mounted relative to said handle element, and moving means, such as one or more rods, for moving the transducer assembly or assemblies, while activated, to any one of a plurality of positions relative to the handle element and relative to tissue to be ablated, whereby ultrasound energy is efficiently delivered to the tissue. The device also includes carrying means, such as a shaft attached at one end to the handle element and having a longitudinal bore therethrough, for carrying the rod or rods and the transducer assembly or assemblies. The rod or rods are engaged with a knob positioned in the handle and when the knob is rotated, the rod or rods are rotated, thereby causing the transducer assembly or assemblies to move relative to the handle, the shaft and the tissue to be ablated.

In one embodiment, the device includes one spool-shaped transducer assembly having a support nut with an internally threaded bore therethrough and a transducer element mounted on the support nut. The transducer element has an arcuate outer surface from which ultrasound energy is emitted. The shaft includes a pair of slots. There is one externally threaded rod rotatably received within the bore of the shaft and the knob is attached to one end of the rod. The transducer assembly is mounted onto the rod and shaft such that the internal threads of the nut engage the external threads of the rod and, when the knob is rotated, the rod is also rotated and the transducer assembly is moved longitudinally along the rod proximate to the slots.

In another embodiment, the device includes four arcuately shaped transducer assemblies, each having a first arcuate surface from which ultrasound energy is emitted in a first general direction and a second arcuate surface, which is positioned opposite the first surface and from which ultrasound energy is emitted in a second general direction which is opposite the first general direction. The shaft has a longitudinal axis and each of the transducer assemblies has a rotational axis that is parallel to the longitudinal axis of the shaft, regardless of the movement of the transducer assemblies. The knob has a central toothed gear attached to it which has an axis of rotation that is parallel to the longitudinal axis of the shaft. There are four rods rotatably received within the bore of the shaft and each has a secondary toothed gear attached to one end thereof and one of the transducer assemblies attached to an opposite end thereof. The secondary gears engage the central toothed gear of the knob such that, when the knob is rotated, each of the secondary gears, the rods and the transducer assemblies are also rotated. The transducer assemblies collectively extend from the distal end of the shaft and conform substantially to the cross-sectional shape of the shaft.

BRIEF DESCRIPTION OF THE DRAWINGS

For a better understanding of the present invention, reference is made to the following detailed description of a preferred embodiment of the present invention considered in conjunction with the accompanying drawings, in which:

FIG. 1A is a schematic perspective view of a concave spool-shaped piezoelectric transducer, which is mounted on a support nut;

FIG. 1B is a schematic cross sectional view of the piezoelectric transducer and nut of FIG. 1A, taken along line A—A and looking in the direction of the arrows;

FIG. 1C is a schematic top plan view of the piezoelectric transducer of FIG. 1A showing the outer boundary of ultrasound energy emitted therefrom;

FIG. 1D is a schematic front elevational view of the piezoelectric transducer of FIG. 1A showing how ultrasound energy is emitted therefrom;

FIG. 2A is a schematic perspective view of a double-faced piezoelectric transducer, including an inner element and an outer element;

FIG. 2B is a schematic top plan view of the double-faced piezoelectric transducer of FIG. 2A showing how ultrasound energy is emitted from each element;

FIG. 2C is a schematic front elevational view of the piezoelectric transducer of FIG. 2A;

FIG. 8 is an enlarged schematic perspective view of the knob and threaded rod of the device of the first embodiment of FIG. 3;

FIG. 9 is an enlarged schematic perspective view of the concave spool-shaped piezoelectric transducer, nut, threaded rod and shaft of the device of the first embodiment of FIG. 3;

FIG. 12 is a schematic side elevational view of the device of the second embodiment of FIG. 10;

FIG. 13 is a schematic top plan view of the device of the second embodiment of FIG. 10, showing the plurality of double-faced piezoelectric transducers in a first position;

FIG. 14 is an enlarged schematic perspective view of the plurality of double-faced piezoelectric transducers of the device of FIG. 13, with a portion of the shaft cut away to show the carrier rods connected to the transducers;

FIG. 15 is a schematic cross sectional view of the device of FIG. 13, taken along line C—C and looking in the direction of the arrows;

FIG. 16 is an enlarged schematic perspective view of the knob, rotatable gears and rods (in phantom) positioned within the handle of the device of FIG. 10 and which are used to move the transducers;

FIG. 17 is a schematic cross sectional view of the knob, rotatable gears and carrier rods of FIG. 16, taken along line D—D and looking in the direction of the arrows;

FIGS. 20A–20G are schematic top plan views of the plurality of double-faced transducers of the device of the second embodiment showing the sequential movements of the transducers between their first and second positions.

DETAILED DESCRIPTION OF THE INVENTION

Figure 3:
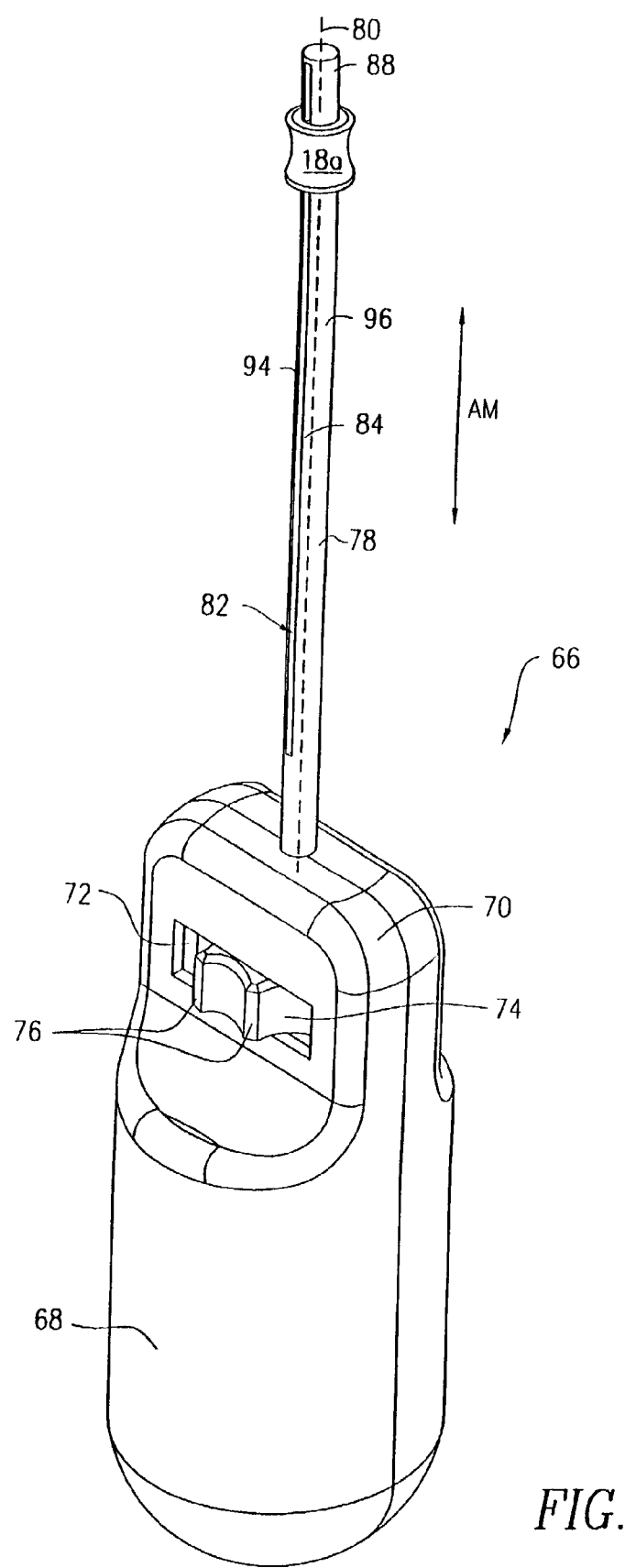
FIG. 3 is a schematic perspective elevational view of a first embodiment of the device of the present invention, which includes a concave spool-shaped piezoelectric transducer and nut similar to that shown in FIG. 1.

The embodiments of the device of the present invention that are described hereinafter each employ piezoelectric transducers for producing and emitting ultrasound energy to perform thermal ablation of tissue of patients in need of such treatment. The basic construction and operation of piezoelectric transducers are well known and understood to those having ordinary skill in the art. However, in order to facilitate the description of the device present invention, the following discussion provides a general description of piezoelectric transducer assemblies of two particular shapes, i.e., spool-shaped and double-faced, that are most suitable for use with the preferred embodiments of the present invention. The transducers of both of these types of transducer assemblies are made of ceramic material such as, PZT4, PZT8, or C5800, each of which is commercially available from ValpeyFischer Corp, Hopkinton, Mass.

With reference initially to FIGS. 1A–1D, a spool-shaped ultrasound transducer assembly 10 in accordance with the present invention (hereinafter referred to as "spool-shaped transducer assembly") is shown schematically from an elevational perspective view (FIG. 1A), from a cross-sectional view (FIG. 1B), from a top plan view (FIG. 1C) and from a side elevational view (FIG. 1D). The spool-shaped transducer assembly 10 includes a hollow spool-shaped piezoelectric transducer 12 (hereinafter referred to as "spool-shaped transducer") mounted on a carrier nut 14.

More particularly, with reference to FIG. 1B, the spool-shaped transducer 12 has an inner surface 16 and an outer surface 18 with a constant, uniform distance therebetween, as measured radially away from the central axis of the transducer. Both the inner and outer surfaces 16, 18 are coated with a conductive coating, such as gold, nickel, gold/chromium, etc., to provide electrical contact with the entire area of each surface 16, 18 while also avoiding electrical contact therebetween. The conductive coatings may be formed by vapor deposition, or any other suitable method that is known and understood to persons having ordinary skill in the art.

The carrier nut 14 has an outer surface 20 which conforms to the shape of the inner surface 16 of the spool-shaped transducer 12. The nut 14 also has an annular ledge 22 for supporting the spool-shaped transducer 12 thereon, as shown most clearly in FIG. 1B. The nut 14 also includes an internally threaded central bore 24 and a pair of arcuate slots 26, 28 for purposes discussed hereinafter.

Referring to FIGS. 1A and 1B, in particular, the inner surface 16 of the spool-shaped transducer 12 is of slightly larger diameter than the outer surface 20 of the nut 14. When the spool-shaped transducer 12 is mounted onto the nut 14 there is an air-filled insulating space 30 between the inner surface 16 of the spool-shaped transducer 12 and the outer surface 20 of the nut 12. Alternatively, any air-filled material, such as styrofoam, can be inserted into the insulating space 30. The purpose of the insulating space 30 is to create an impedance mismatch between the inner surface 16 of the spool-shaped transducer 12 and the air layer within the insultaing space 30, such that the spool-shaped transducer 12 will emit ultrasound energy only radially outward from the outer surface 18 when activated.

As shown schematically in FIG. 1B, an electrically conductive wire 32 is connected at one end thereof to the inner surface 16 of the spool-shaped transducer 12 and another electrically conductive wire 34 is connected at one end thereof to the outer surface 18 of the spool-shaped transducer 12. The wires 32, 34 are each, preferably, a component of a coaxial cable (not shown) and are connected at their opposite ends to a source of electrical voltage, more particularly, an RF power source 36 (shown schematically only in FIG. 1B) so that a radiofrequency (RF) electrical voltage can be applied to the spool-shaped transducer 12. The RF power source 36 typically operates at about 1–12 MHz. The arrows in FIG. 1C show, schematically, the radial and circumferential paths of acoustic energy that are created when the spool-shaped transducer 12 is activated by applying an RF voltage thereto. More particularly, in operation, an acoustical wave of ultrasound energy is emitted radially outward from the entire outer surface 18 of the spool-shaped transducer 12, in a direction perpendicular to the outer surface 18 (see arrows in FIG. 1C). Since the outer surface 18 of the spool-shaped transducer 12 is concave (see FIGS. 1A, 1B and 1D), the ultrasound energy is emitted in a focal zone (FIG. 1D) having an outer boundary that defines a circle FZ about the spool-shaped transducer assembly 10 (see FIGS. 1C and 1D). It is noted that the three-dimensional shape of the aforesaid focal zone approximates a toroid (not shown).

With reference now to FIGS. 2A–2C, a double-faced piezoelectric transducer assembly 38 (hereinafter referred to as "double-faced transducer assembly") is shown schematically from an elevational perspective view (FIG. 2A), from a top plan view (FIG. 2B) and from a front elevational view (FIG. 2C). More particularly, the double-faced transducer assembly 38 includes a first transducer element 40 and a second transducer element 42. The first transducer element 40 has a first surface 44 and an opposite second surface 46, both of which are coated with a conductive coating, such as gold, nickel, gold/chromium, etc., to provide electrical contact with the entire area of each surface 44, 46, while also avoiding electrical contact therebetween. Similarly, the second transducer element 42 has a first surface 48 and an opposite second surface 50 that are coated with a conductive coating, such as gold, nickel, gold/chromium, etc., to provide electrical contact with the entire area of each surface 48, 50, while also avoiding electrical contact therebetween.

In a manner similar to that described hereinabove in connection with the spool-shaped transducer 12, electrically conductive wires 52, 54, which are each preferably components of a coaxial cable (not shown), are connected to the first surface 44 and the second surface 46, respectively, of the first transducer element 40. The electrically conductive wires 52, 54 are also connected to a source of electrical voltage, more particularly, an RF power source 56 (shown schematically only in FIG. 2A) so that a radiofrequency (RF) electrical current can be applied to the first transducer element 40. Similarly, two additional electrically conductive wires 48, 50, are connected to the first surface 48 and the second surface 50, respectively, of the second transducer element 42 and to a source of electrical voltage, more particularly, an RF power source 62 (shown schematically only in FIG. 2A) so that a radiofrequency (RF) electrical current can be applied to the second transducer element 42. It is noted that suitable RF power can be supplied individually to each of the first and second transducer elements 40, 42 by a single multi-channel RF power source (not shown, but known to those of ordinary skill in the art). The RF power sources 56, 62 each typically operate at about 1–12 MHz.

As shown most clearly in FIGS. 2A and 2B, the double-faced transducer assembly 38 is assembled by mounting the first and second transducer elements 40, 42 adjacent to, but without contacting, one another. More particularly, it will be noted that the first and second transducer elements 40, 42 are each sized and shaped such that the second surface 46 of the first transducer element 40 has approximately the same configuration and surface area as the first surface 48 of the second transducer element 42 so that the first and second transducer elements 40, 42 can be mounted adjacent to one another, with an air-filled insulating space 64 between them. If it is desired to leave the insulating space 64 filled with air only, the first and second transducer elements 40, 42 can be connected to one another by a sealing strip (not shown) of air-tight material, such as silicone, that is deposited at the edges of the first and second transducer elements 40, 42, about the perimeter of the insulating space 64. Alternatively, any air-filled material, such as styrofoam, can be inserted into the insulating space 64.

The purpose of the insulating space 64 is to create an impedance mismatch at the surfaces 46, 48 of each of the first and second transducer elements 40, 42, respectively, that are adjacent to the insulating space 64. More particularly, the impedance mismatch causes the first transducer element 40 to emit ultrasound energy only radially outward from its first surface 44 when activated and causes the second transducer element 42 to emit ultrasound energy only radially outward from its second surface 50 when activated. It is further noted that each double-faced transducer assembly 38 is sized and shaped such that four similar double-faced transducers can be arranged with one another to approximate the shape of a cylindrical transducer (see, for example, FIGS. 10 and 14).

In operation, as shown schematically by the arrows in FIG. 2B, when the first transducer element 40 of a double-faced transducer assembly 38 is activated by applying an RF voltage to the first transducer element 40, an acoustical wave of ultrasound energy is emitted radially outwardly from the entire first surface 44 of the first transducer element 40 in a direction perpendicular to the first surface 44 (see FIG. 2B), converging at a focal zone FZ'. Similarly, when the second transducer element 42 of a double-faced transducer assembly 38 is activated by applying an RF voltage to the second transducer element 42, an acoustical wave of ultrasound energy is emitted radially outwardly from the entire second surface 50 of the second transducer element 42, in a direction perpendicular to the second surface 50 (see FIG. 2B).

When ultrasound energy is absorbed by tissue, it is converted into heat and, therefore, the tissue becomes heated. For example, with reference to the spool-shaped transducer assembly 10, RF power is supplied by the RF power source 36 to the spool-shaped transducer 12, at the resonant frequency of the spool-shaped transducer 12 which activates the spool-shaped transducer to emit ultrasound energy. The resonant frequency of the spool-shaped transducer 12 is proportional to the thickness of the spool-shaped transducer 12 between the inner and outer surfaces 16, 18 thereof. Typically, for use in connection with the present invention, the spool-shaped transducer 12 and the first and second transducer elements 40, 42 should each be constructed having resonant frequencies ranging between about 2 to 12 MHz, preferably about 5 MHz. It is noted that the direction of ultrasound energy emissions from the spool-shaped transducer 12 and from the first and second transducer elements 40, 42 are easier to control than the direction of RF energy emissions from bipolar or monopolar RF devices known in the prior art. This is partly because the ultrasound energy emissions are directional from the source and partly because their direction of travel does not depend upon the placement of an antipolar electrode or ground plate, nor on tissue electrical properties that vary with tissue dessication that occurs during ablation. Since the spool-shaped transducer 12 and the first and second transducer elements 40, 42 are directional, repositioning them will alter the direction of the ultrasonic acoustic field created thereby and will also, therefore, redirect the tissue heating.

Since both embodiments of the device of the present invention include one or more piezoelectric transducer assemblies of the two general types described hereinabove (i.e., spool-shaped and double-faced), and because the transducer assemblies are constructed and operated as described hereinabove, the transducer assemblies and their components shown in FIGS. 3–20G are labeled using variations of the reference numbers used in FIGS. 1A–1D and 2A–2C. For example, where the embodiment being discussed includes one or more spool-shaped transducer assemblies like that described hereinabove, they will be labeled using reference number "10" followed by a lower-case letter, for example, 10a, 10b, 10c, etc. Where the embodiment being discussed includes one or more double-faced transducer assemblies like that described hereinabove, they will be labeled using reference number "36" followed by a lower-case letter, for example 36a, 36b, 36c, etc. In addition, where the terms "distal" and "proximal" are used hereinafter in connection with the device of the present invention or components thereof, these terms refer to positions that are relative to the user (hereinafter "surgeon") operating the device.

Figure 4:
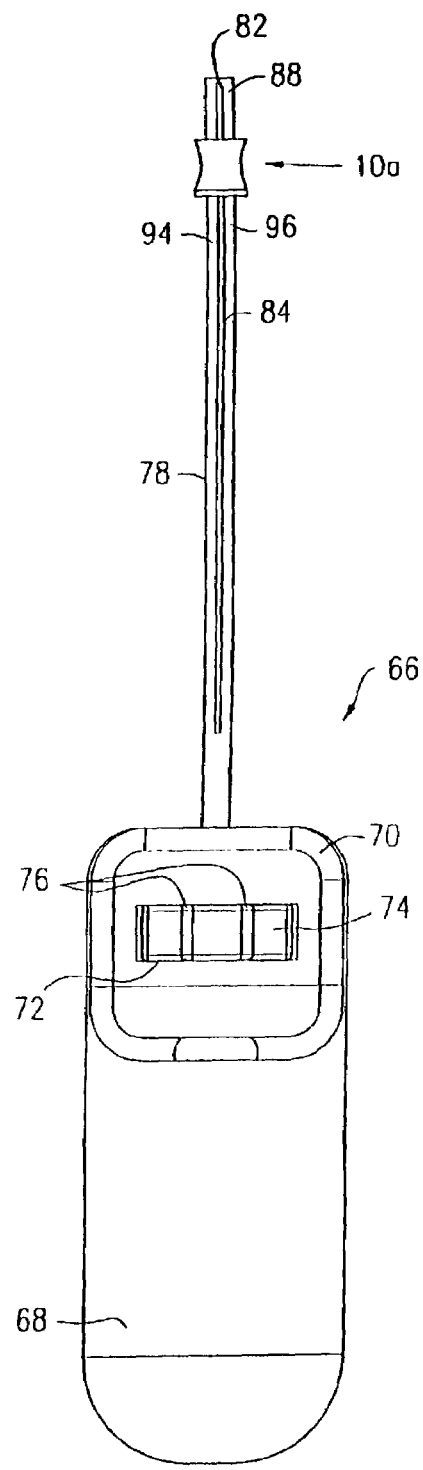
FIG. 4 is a schematic front elevational view of the device of the first embodiment of FIG. 3.
Figure 5:
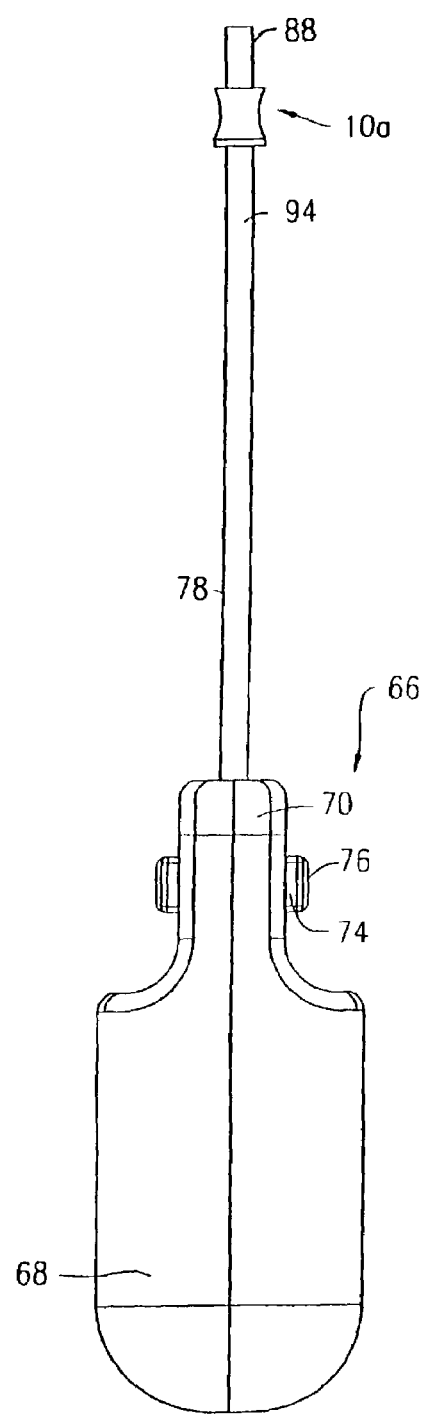
FIG. 5 is a schematic side elevational view of the device of the first embodiment of FIG. 3.
Figure 6:
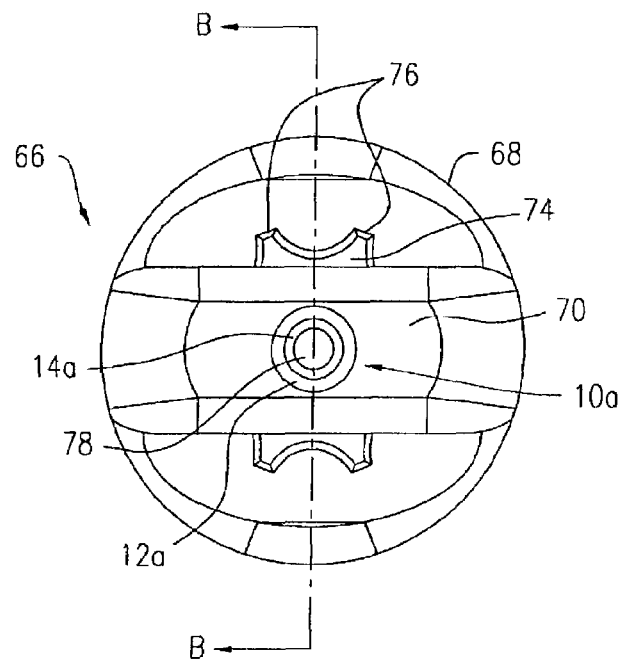
FIG. 6 is a schematic top plan view of the device of the first embodiment of FIG. 3.

With reference now to FIGS. 3–9, a first embodiment of a device 66 in accordance with the present invention is shown. The device 66 is shown schematically in a perspective elevational view (FIG. 3), in a front elevational view (FIG. 4) and in a side elevational view (FIG. 5). More particularly, as shown in FIGS. 3–5, the device 66 includes a handle element 68 which is sized and shaped to be held by a surgeon performing thermal ablation therapy during placement and operation of the device 66, as will be described in further detail hereinafter. The handle element 68 includes a bridge portion 70 having a transversely oriented cutout opening 72 therethrough. A controller, such as a rotatable knob 74 with finger grips 76, is positioned within the cutout opening 72. The rotatable knob 74 is sized and shaped such that the finger grips 76 protrude at least partially out of the cutout opening 72 (see FIGS. 3, 6 and 8) to be accessible for contact and manipulation by the surgeon's fingers.

As shown in FIGS. 3–5, the device 66 also includes a carrier, such as an elongated shaft 78, that is attached to the bridge portion 70 of the handle element 68 and extends axially therefrom. The shaft 78 has a central longitudinal axis 80 and a longitudinal bore 82 that is substantially aligned with the central longitudinal axis 80. The shaft 78 also has a pair of longitudinal slots 84, 86 (only one of which, 84, can be seen in the figures) that are positioned opposite one another on the shaft 78. The longitudinal slots 84, 86 are both oriented parallel to the central longitudinal axis 80 of the shaft 78 and are in communication with the longitudinal bore 82 (see, e.g., FIGS. 3, 4 and 9). As discussed in further detail hereinafter, the shaft 78 is sized and shaped to be inserted, distal end 88 first, into any of the various cavities and luminal structures of a patient's body where tissue requiring thermal ablation therapy may be located.

Figure 7:
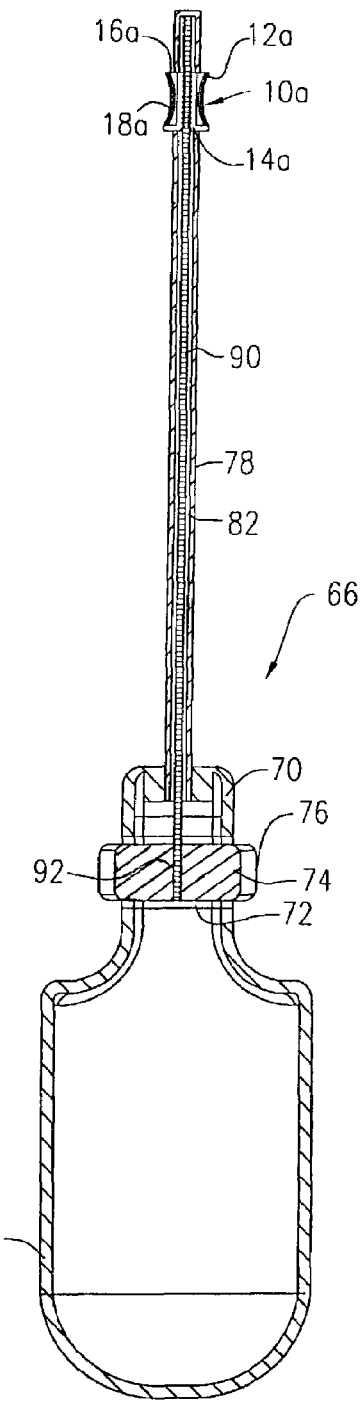
FIG. 7 is a schematic cross sectional view of the device of the first embodiment of FIG. 6, taken along line B—B and looking in the direction of the arrows.

In addition, as shown in FIGS. 7–9, the device 66 includes moving means, such as a rod 90 having external threads, that is rotatably received within the longitudinal bore 82 of the shaft 78. The rod 90 extends from the distal end 88 of the shaft 78, through the longitudinal bore 82 and through a hole (not shown) provided in the bridge portion 70 of the handle element 68. The hole (not shown) is in communication with the longitudinal bore 82 of the shaft 78. Thus, as shown in FIG. 8, the proximal end 92 of the threaded rod 90 extends into the cutout opening 72 and is attached to the rotatable knob 74 (see FIG. 8) such that rotation of the knob 74 also causes rotation of the rod 90, for a purpose which will become clear hereinafter.

A spool-shaped transducer assembly 10a is moveably mounted on the shaft 78 and the rod 90, as follows. With reference to FIGS. 4 and 9, in particular, the two portions 94, 96 of the shaft 78 located between the longitudinal slots 84, 86 are each received through a corresponding arcuate slot 24a, 26a of the nut 14a (see FIG. 9). In addition, the internal threads of the nut 14a are engaged with the external threads of the rod 90, such that when the rod 90 is rotated, the spool-shaped transducer assembly 10a is moved axially along the shaft 78 in the directions shown by the arrow AM in FIG. 3. It is noted that the lengths of the slots 84, 86 of the shaft 78 determine the maximum axial limitations of the movement of the spool-shaped transducer assembly 10a along the shaft 78 and rod 90.

It is noted that, although not specifically shown in the figures, the spool-shaped transducer assembly 10a has a pair of electrically conductive wires (not shown) that are connected to their inner and outer surfaces 16a, 18a of the spool-shaped transducer 12a, as well as to one or more RF power sources (not shown), as described hereinabove in connection with the construction and operation of the generic spool-shaped transducer assembly 10. To protect the wires, which are preferably coaxial cables (not shown), and minimize interference with the manipulation and operation of the device 66 by the surgeon, the aforesaid wires (not shown) can be attached to the spool-shaped transducer 12a and extended through the longitudinal bore 82 of the shaft 78 to the RF power source or sources. The RF power source or sources may be located within, or external to, the handle element 68.

With reference to the overall size and shape of the device 66, it is noted that the device 66 is intended for use to perform thermal ablation of tissue located within or proximate to any of the various cavities or luminal structures of a patient's body. Thus, the shaft 78 of the device 66, which carries the rod 90 and spool-shaped transducer assembly 10a, is sized and shaped to be inserted and positioned within the cavities and luminal structures of a patient's body. More particularly, depending upon the size and shape of the particular cavities and luminal structures to be entered by the device 66, the outer diameter of the shaft 78 should be between about 0.2 centimeters ("cm") and 1.0 cm, preferably 0.4 cm. The diameter of the longitudinal bore 82 of the shaft 78 should be large enough to rotatably receive the rod 90 and the conductive wires (not shown) attached to the spool-shaped transducer 12a therethrough, and more particularly, from about 0.1 cm to 0.4 cm, preferably about 0.4 cm. The length of the shaft 78 should be sufficient so that the spool-shaped transducer assembly 10a can be inserted far enough into the cavity or luminal structure to be positioned proximate to the tissue requiring thermal ablation. Such length will vary depending upon the cavity of luminal structure involved, but will, in most cases, be somewhere between about 10.0 cm and 40.0 cm. Since the shaft 78 is inserted into the patent's body and must carry the rod 90 and the spool-shaped transducer assembly 10a, it should be made of substantially rigid surgical grade material, such as stainless steel or surgical polymers.

With reference to the rod 90, it should have an outer diameter that is small enough to allow the rod 90 to fit rotatably within the longitudinal bore 82 of the shaft 78. In addition, the rod 90 should be made of surgical grade material, such as stainless steel or surgical polymers, having sufficient resilience to remain substantially rigid and to bear external threads thereon that are not easily deformed. The rod 90 should also be long enough to extend from the distal end 88 of the shaft 78, through the longitudinal bore 82 of the shaft 78, and into the cutout opening 72 of the handle element 68, which is approximately 15 cm to 50 cm, preferably approximately 25 cm.

The handle element 68 of the device 66, which remains substantially external to the patient's body, should be sized and shaped to fit comfortably within the hand of a surgeon, while allowing the surgeon's fingers to comfortably extend to and manipulate the rotatable knob 74. For example, the handle element 68 may be approximately 12 cm to 20 cm long and approximately 2.5 cm to 4.0 cm wide or thick. The handle element 68 may be hollow, as in the present embodiment. Although the handle element 68 remains substantially outside the patient's body, it should still be made of a substantially rigid surgical grade material, such as such as stainless steel or surgical polymers.

The spool-shaped transducer assembly 10a should be sized and shaped to allow it to be moveably carried on the shaft 78 and rod 90, such that it can be positioned and moved within a cavity or luminal structure, after insertion into the cavity or luminal structure and while activated and emitting ultrasound energy. In the present embodiment of the device 66, the spool-shaped transducer assembly 10a is between about 1.0 and 3.0 cm long, preferably about 2.0 cm long. In addition, the spool-shaped transducer assembly 10a is about 0.5 cm to 2.0 cm wide at its greatest diameter. It is noted that the spool-shaped transducer assembly 10a remains proximate to the shaft 78, regardless of its position on the shaft 78 during movement. This arrangement allows movement of the spool-shaped transducer assembly 10a, relative to the shaft 78, the handle 68 and the tissue to be ablated, even after insertion and placement into the cavity or luminal structure of the patient's body. Furthermore, the spool-shaped transducer 10a can be moved while the spool-shaped transducer assembly 10a is activated and emitting ultrasound energy. Such movement of the spool-shaped transducer assembly 10a is possible without having to move the handle element 68 or reposition the shaft 78, which simplifies the procedure for the surgeon and also minimizes patient discomfort during the procedure.

In the foregoing arrangement, during operation of the device 66, ultrasound energy is emitted by the spool-shaped transducer assembly 10a in a radially outward direction, with a focal zone having a specific determinable outer boundary FZ (see, for example, FIGS. 1C and 1D). The method of operating the device 66 in accordance with the present invention, as well as the advantages achieved thereby, will be described in further detail hereinafter.

Initially, it is noted that, in operation, the device 66 of the present invention may be used in conjunction with a fluid-filled balloon, such as is well-known in the art for treating the endometrium (inner lining of the uterine cavity). Alternatively, the device 66 may be used without such a balloon and, instead the cavity or luminal structure should be filled with enough fluid to contact the tissue to be ablated and to submerge the spool-shaped transducer assembly 10a which is positioned proximate to the tissue. The fluid is required to provide a medium for the ultrasound energy emitted from the ultrasound transducers to travel to, and be absorbed by, the tissues to be treated. For purposes of the following discussion, the cavity or luminal structure will be prepared for surgery and filled with a suitable fluid, such as saline, in a manner that is well-known to those of ordinary skill in the art and consistent with currently accepted medical/surgical standards.

Prior to activating the spool-shaped transducer 10a, the surgeon grips the handle element 68 of the device 66 and inserts the shaft 78, with the rod 90 carried therein and the spool-shaped transducer assembly 10a mounted thereon, into a cavity or luminal structure. The handle element 68 is moved, which, in turn, also moves the shaft 78, until the longitudinal slots 84, 86 of the shaft 78 are proximate to at least a portion of the tissue in need of thermal ablation. The surgeon then turns the rotatable knob 74, which rotates the rod 90, which, in turn, moves the spool-shaped transducer assembly 10a. The knob 74 is turned until the spool-shaped transducer assembly 10a is proximate to at least a portion of the tissue to be ablated such that the tissue is located within the focal zone of the spool-shaped transducer assembly 10a. The RF power source (not shown) is then turned on to activate the spool-shaped transducer 12a which then emits ultrasound energy that is, in turn, transmitted to the tissue, thereby heating the tissue.

After a clinically determined period of time, which will depend upon the nature and size of the tissue area being ablated and its distance from the spool-shaped transducer 12a, the knob 74 is again turned and the spool-shaped transducer assembly 10a is thereby moved to another location on the shaft 78 such that additional tissue to be ablated is within the focal zone of the spool-shaped transducer assembly 10a. Typically, the clinically determined period of time for which the spool-shaped transducer assembly 10a remains activated proximate to a particular tissue area will be between about 5 and 20 seconds, but should be no more than about 60 seconds, and should preferably be from about 10 to 20 seconds. The spool-shaped transducer assembly 10a is moved, in the foregoing manner, as many times as necessary to achieve the desired pattern of heating. After the desired pattern of heating is achieved, the RF power source is turned off.

It is noted that the desired pattern of heating will be determined by the surgeon, based upon clinical factors and experience. For example, depending upon the overall size of the tissue area in need of thermal ablation and the size of the focal zone created by the activated spool-shaped transducer assembly 10a, there may be only one tissue area to be directly ablated, which would require no repositioning of the spool-shaped transducer assembly 10a while activated. Alternatively, there may be a number of tissue areas to be ablated, which would require that the spool-shaped transducer assembly 10a be moved a number of times while activated. In addition, where there are multiple areas of tissue to be ablated, they may be adjacent to one another or not, depending upon the type of tissue, the cavity or the luminal structure being affected by the ablation. Where the tissue areas to be ablated are not adjacent to one another, the RF power source (not shown) may be turned off before moving the spool-shaped transducer assembly 10a (by turning the knob 74) to a new position on the shaft 78 proximate to the next tissue area to be ablated, and then turned back on. This procedure would minimize heating of tissue areas that are not in need of ablation. Additionally, the RF power supplied to the spool-shaped transducer assembly 10a may be adjusted to be more or less such that the time required at a target location will be shorter or longer, respectively.

With reference now to FIGS. 10–20G, a second embodiment of a device 98 in accordance with the present invention is shown. More particularly, the device 98 is shown schematically in a perspective elevational view (FIG. 10), in a front elevational view (FIG. 11) and in a side elevational view (FIG. 12). The device 98 includes a handle element 100 which is sized and shaped to be held by a surgeon performing thermal ablation therapy during placement and operation of the device 98, as will be described in further detail hereinafter. The handle element 100 includes a bridge portion 102 having a transversely oriented cutout opening 104 therethrough. The handle element 100 also includes a fixed knob 106 with finger grips that is positioned proximate to the bridge portion 102 and which facilitates manipulation of the device 98 by the surgeon.

Figure 10:
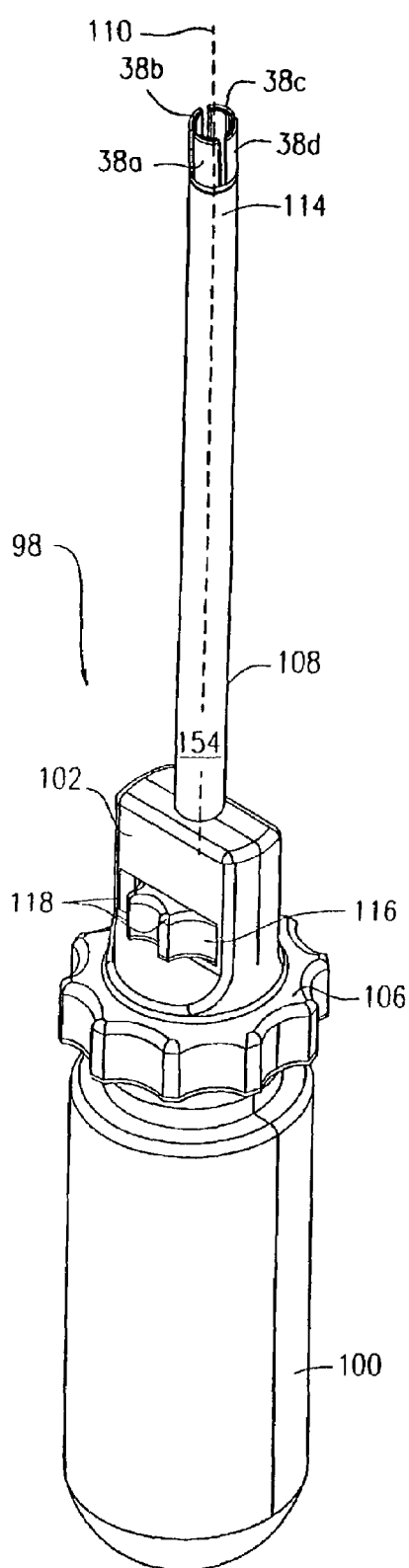
FIG. 10 is a schematic perspective elevational view of a second embodiment of the device of the present invention, including a plurality of double-faced piezoelectric transducers.
Figure 11:
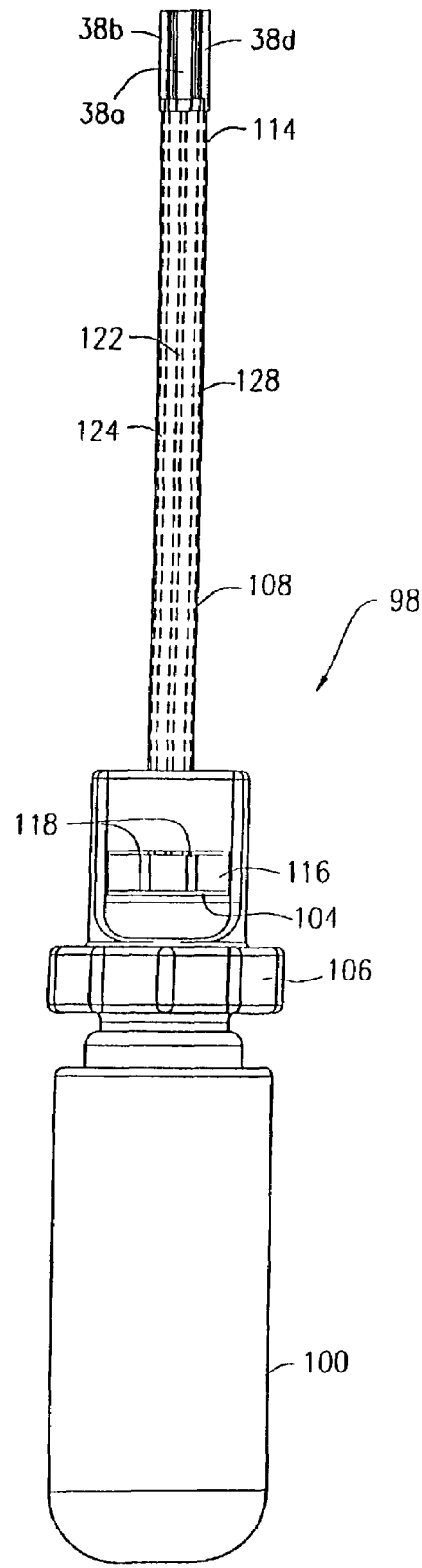
FIG. 11 is a schematic front elevational view of the device of the second embodiment of FIG. 10.
Figures 18, 19:
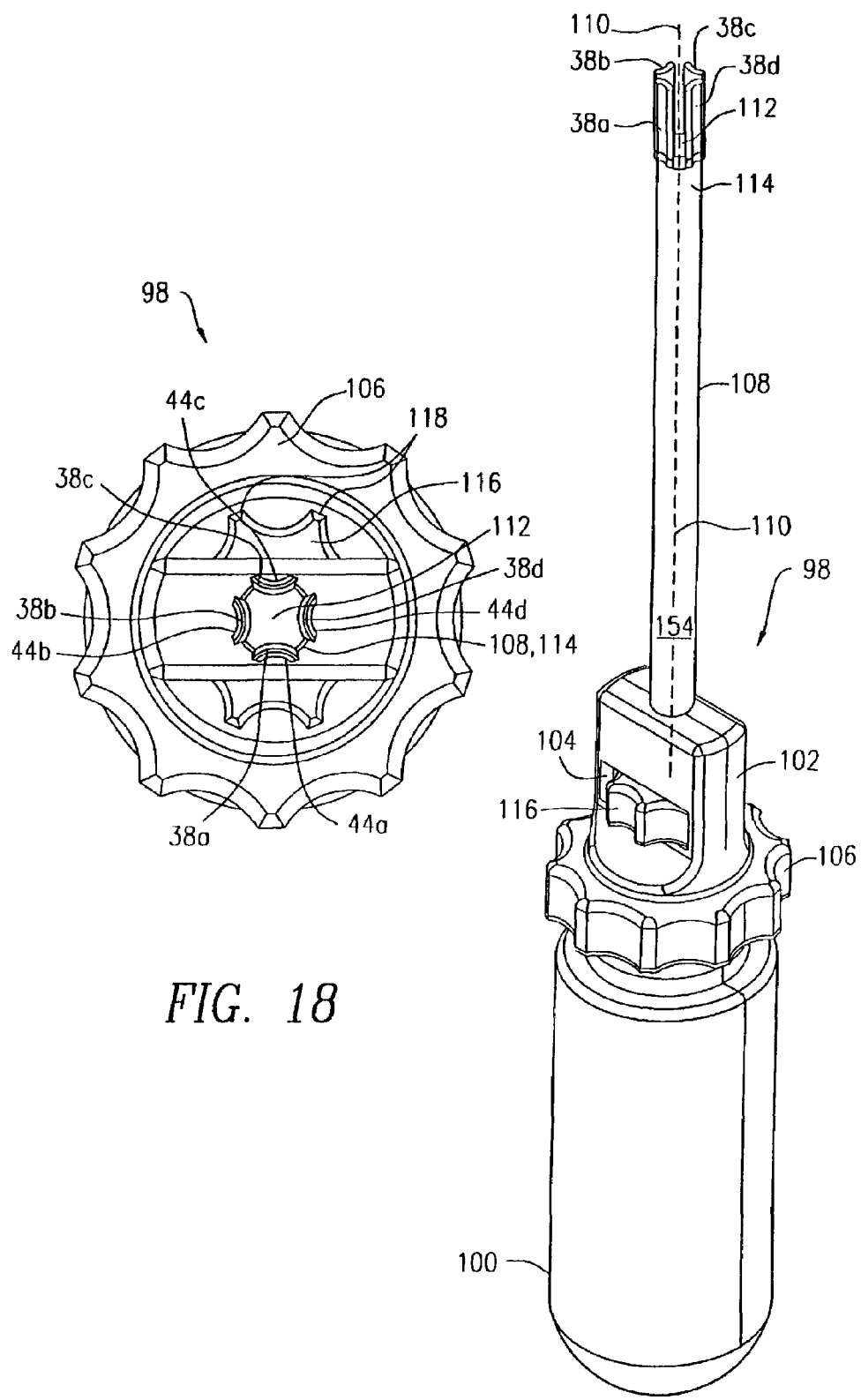
FIG. 18 is a schematic top plan view of the device of the second embodiment of FIG. 10, showing the plurality of double-faced piezoelectric transducers in a second position.
FIG. 19 is a schematic perspective elevational view of the device of the second embodiment of FIG. 10, showing the plurality of double-faced piezoelectric transducers in the second position.

With reference still to FIGS. 10–12, the device 98 further includes a carrier, such as an elongated shaft 108, that is attached to the bridge portion 102 of the handle element 100 and extends axially therefrom. The shaft 108 has a central longitudinal axis 110 and a longitudinal bore 112 that is substantially aligned with the central longitudinal axis 110. As discussed in further detail hereinafter, the shaft 108 is sized and shaped to be inserted, distal end 114 first, into any of the various cavities and luminal structures of a patient's body where tissue requiring thermal ablation therapy may be located.

With reference still to FIGS. 10–12, a controller, such as a rotatable knob 116 with finger grips 118, is positioned within the cutout opening 104 of the handle element 100. The rotatable knob 116 is sized and shaped such that the finger grips 118 protrude at least partially out of the cutout opening 104 (see FIGS. 10, 12 and 13) to be accessible for contact and manipulation by the surgeon's fingers. A central toothed gear 120 is affixed to the rotatable knob 116 proximate to the shaft 108 such that the rotational axes (not shown) of the rotatable knob 116 and the central gear 120 are aligned with one another and with the central longitudinal axis 110 of the shaft 108.

In addition, with reference in particular to FIGS. 11, 15 and 16, the device 98 includes moving means, which, in the present embodiment, includes four rods 122, 124, 126, 128 that are rotatably received within the longitudinal bore 112 of the shaft 108. Each of the rods 122, 124, 126, 128 extends from the distal end 114 of the shaft 108, through the longitudinal bore 112, to the bridge portion 102 of the handle element 100. Thus, as shown in FIGS. 15 and 16, the proximal end 130, 132, 134, 136 of each of the rods 122, 124, 126, 128, respectively, extends into the cutout opening 104 and is attached to a corresponding secondary toothed gear 138, 140, 142, 144. It is noted that the rotational axes (not shown) of each of the secondary gears 138, 140, 142, 144 are substantially parallel to the central longitudinal axis 110 of the shaft 108. In the foregoing arrangement, rotation of the secondary gears 138, 140, 142, 144 will cause rotation of each of the rods 122, 124, 126, 128, respectively, for a purpose which will become clear hereinafter. Moreover, as shown most clearly in FIGS. 15 and 16, the secondary gears 138, 140, 142, 144 are arranged about, and are engaged with, the central gear 120 such that rotatation of the central gear 120 will cause synchronous rotation of the secondary gears 138, 140, 142, 144 and, in turn, the rods 122, 124, 126, 128 attached thereto.

The device 98 also includes four double-faced transducer assemblies 38a, 38b, 38c, 38d that are located proximate, but unconnectedly, to the distal end 114 of the shaft 108. As shown in FIGS. 10–14, the double-faced transducer assemblies 38a, 38b, 38c, 38d are oriented relative to the shaft 108 such they form a substantially cylinder-shaped extension of the shaft 108 having approximately the same outer diameter as the shaft 108 (see, especially, FIG. 14). As shown in FIGS. 14 and 15, each of the double-faced transducer assemblies 38a, 38b, 38c, 38d is securely attached to the distal end 146, 148, 150, 152 of one of the rods 122, 124, 126, 128. In this manner, as will be discussed in further detail hereinafter, the double-faced transducer assemblies 38a, 38b, 38c, 38d extend substantially axially from the distal end of the shaft 108 and, when rotationally moved, they protrude only minimally beyond the outer surface 154 of the shaft 108 (see FIGS. 18 and 19). It is noted that, in the foregoing arrangement, rotation of the rods 122, 124, 126, 128 will also rotate each of the double-faced transducer assemblies 38a, 38b, 38c, 38d (as shown in FIGS. 20A–20G).

With reference to FIGS. 10, 13, 18, 19 and 20A–20G, and to FIGS. 20A–20G, in particular, it is noted that the double-faced transducer assemblies 38a, 38b, 38c, 38d are rotatable 360 degrees such that their energy-emitting surfaces 44a, 44b, 44c, 44d, 50a, 50b, 50c, 50d, can be made to face inward (see FIGS. 10, 13 and 20A), or outward (see FIGS. 18, 19 and 20G), or any of a number of intermediate directions (see, for example, FIGS. 20B–20F). More particularly, rotation of the double-faced transducer assemblies 38a, 38b, 38c, 38d is achieved as follows. The surgeon rotates the rotatable knob 116 which, in turn, causes the central gear 120 to rotate. Rotation of the central gear 120 causes synchronous rotation of the secondary gears 138, 140, 142, 144, which rotates the rods 122, 124, 126, 128 attached thereto. Rotation of the rods 122, 124, 126, 128 results in rotation of the double-faced transducer assemblies 38a, 38b, 38c, 38d. When the double-faced transducer assemblies 38a, 38b, 38c, 38d are oriented (i.e., when their energy-emitting surfaces 44a, 44b, 44c, 44d, 50a, 50b, 50c, 50d are oriented) in an effective position, as determined by the surgeon based upon clinical factors and experience, the surgeon will stop rotating the rotatable knob 116, which, in turn, ceases rotation of the other components, including the double-faced transducer assemblies 38a, 38b, 38c, 38d. In the foregoing manner, any one of a number of orientations of the double-faced transducer assemblies 38a, 38b, 38c, 38d can be achieved. In addition, it is noted that the double-faced transducer assemblies 38a, 38b, 38c, 38d can be moved and rotated as described above after insertion and placement within a patient's cavity or luminal structure and while the double-faced transducer assemblies 38a, 38b, 38c, 38d are activated and emitting ultrasound energy.

It is noted that, although not specifically shown in the figures, as described hereinabove in connection with the construction and operation of the generic double-faced transducer assembly 38, each first transducer element 40a, 40b, 40c, 40d of each double-faced transducer assembly 38a, 38b, 38c, 38d, respectively, has a pair of electrically conductive wires (not shown) that are connected to its first and second surfaces 44a, 44b, 44c, 44d, 46a, 46b, 46c, 46d and to one or more RF power sources (not shown). Similarly, each second transducer element 42a, 42b, 42c, 42d of each double-faced transducer assembly 38a, 38b, 38c, 38d, respectively, has a pair of electrically conductive wires (not shown) that are connected to its first and second surfaces 48a, 48b, 48c, 48d, 50a, 50b, 50c, 50d and to one or more RF power sources (not shown). To protect the wires, which are preferably coaxial cables (not shown), and minimize interference with the manipulation and operation of the device 98 by the surgeon, the aforesaid wires (not shown) can be attached to the double-faced transducer assemblies 38a, 38b, 38c, 38d, as described, and extended through the longitudinal bore 112 of the shaft 108 to the RF power source or sources. The RF power source or sources may be located within, or external to, the handle element 100.

It addition, as will be understood by persons having ordinary skill in the art, the RF source or sources (not shown) may have multiple individual channels such that the power level supplied to each of the first and second transducer elements 40a, 40b, 40c, 40d, 42a, 42b, 42c, 42d of each of the double-faced transducer assemblies 38a, 38b, 38c, 40d, respectively, can be individually controlled. With such a configuration, it is possible to cause only certain double-faced transducer assemblies 38a, 38b, 38c, 38d (or energy-emitting surfaces 44a, 44b, 44c, 44d, 50a, 50b, 50c, 50d thereof) to emit ultrasound energy, or to emit different levels of ultrasound energy, as desired based upon clinical conditions, including the nature, size and location of the tissue to be ablated. The first and second transducer elements 40a, 40b, 40c, 40d, 42a, 42b, 42c, 42d may also be "multiplexed" such that a single RF power source is sequentially switched among the first and second transducer elements 40a, 40b, 40c, 40d, 42a, 42b, 42c, 42d. In certain situations, as shown for example shown in FIG. 13, only surfaces 44a, 44b, 44c, 44d of the double-faced transducer assemblies 38a, 38b, 38c, 38d would be activated to emit ultrasound energy radially outward from the device 98. Alternatively, as shown for example in FIG. 18, only surfaces 50a, 50b, 50c, 50d of the double-faced transducer assemblies 38a, 38b, 38c, 38d would be activated to emit ultrasound energy radially outward from the device 98.

With reference to the overall size and shape of the device 98, it is noted that the device 98 of the second embodiment is intended for use to perform thermal ablation of tissue located within or proximate to any of the various cavities or luminal structures of a patient's body. Thus, the shaft 108 of the device 98, which carries the rods 122, 124, 126, 128 and the double-faced transducers assemblies 38a, 38b, 38c, 38d, is sized and shaped to be inserted and positioned within the cavities and luminal structures of a patient's body. More particularly, depending upon the size and shape of the particular cavities and luminal structures to be entered by the device 98, the outer diameter of the shaft 108 should be between about 0.5 centimeters ("cm") and 1.5 cm, preferably 1.0 cm. The diameter of the longitudinal bore 112 of the shaft 108 should be large enough to rotatably receive the rods 122, 124, 126, 128 and the conductive wires (not shown) attached to the double-faced transducer assemblies 38a, 38b, 38c, 38d therethrough, and more particularly, from about 0.4 cm to 1.3 cm, preferably about 0.8 cm.

The length of the shaft 108 should be sufficient so that the double-faced transducer assemblies 38a, 38b, 38c, 38d can be inserted far enough into the cavity or luminal structure to be positioned proximate to the tissue requiring thermal ablation. Such length will vary depending upon the cavity of luminal structure involved, but will, in most cases, be somewhere between about 15 cm and 45 cm. Since the shaft 108 is inserted into the patent's body and must carry the rods 122, 124, 126, 128 and the double-faced transducer assemblies 38a, 38b, 38c, 38d, it should be made of substantially rigid surgical grade material, such as stainless steel or surgical polymers.

With reference to the rods 122, 124, 126, 128, they should each have an outer diameter that is small enough to allow all of the rods 122, 124, 126, 128 to fit rotatably within the longitudinal bore 112 of the shaft 108 without interfering with one another's rotational movement. In addition, the rods 122, 124, 126, 128 should be made of substantially rigid surgical grade material, such as stainless steel or surgical polymers. The rods 122, 124, 126, 128 should each be long enough to extend from the distal end 114 of the shaft 108, through the longitudinal bore 112 of the shaft 108, and into the cutout opening 104 of the handle element 100. More particularly, the length of each of the rods 122, 1224, 126, 128 should be approximately 17 cm to 47 cm, which, it is noted, is a slightly longer that the shaft 108.

The handle element 100 of the device 98, which remains substantially external to the patient's body, should be sized and shaped to fit comfortably within the hand of a surgeon, while allowing the surgeon's fingers to comfortably extend to and manipulate the rotatable knob 116. For example, the handle element 100 may be approximately 8 cm to 12 cm long and approximately 4 cm to 6 cm wide or thick. The handle element 100 may be hollow, as in the present embodiment. Although the handle element 100 remains substantially outside the patient's body, it should still be made of a substantially rigid surgical grade material, such as such as stainless steel or surgical polymers.

Each of the double-faced transducer assemblies 38a, 38b, 38c, 38d must be sized and shaped such that they can be positioned and moved, relative to the shaft 108 and handle element 100, after insertion into the cavity or luminal structure and while activated and emitting ultrasound energy. In addition, each of the double-faced transducer assemblies 38a, 38b, 38c, 38d should be sized and shaped approximately the same as one another such that, when mounted on the rods 122, 124, 126, 128 and positioned proximate to the distal end 114 of the shaft 108, they form a substantially cylindrical extension of the shaft 108 having a diameter approximately the same as the outer diameter of the shaft 108 (see FIGS. 10–14). In the present embodiment of the device 98, each double-faced transducer assembly 38a, 38b, 38c, 38d is between about 0.5 and 2.0 cm long, preferably about 1.2 cm long. In addition, each double-faced transducer assembly 38a, 38b, 38c, 38d is about 0.3 cm to 1.0 cm wide and about 0.07 cm to 0.45 cm thick (i.e., the distance measured between the first surface 44a, 44b, 44c, 44d of the first transducer element 40a, 40b, 40c, 40d, respectively, and the second surface of the 50a, 50b, 50c, 50d of the second transducer element 42a, 42b, 42c, 42d, respectively). It is noted that each double-faced transducer assembly 38a, 38b, 38c, 38d remains proximate to the shaft 108, regardless of its orientation during movement. This arrangement allows movement of each double-faced transducer assembly 38a, 38b, 38c, 38d, relative to the shaft 108, the handle 100 and the tissue to be ablated, even after insertion and placement into the cavity or luminal structure of the patient's body. Furthermore, each double-faced transducer assembly 38a, 38b, 38c, 38d can be moved while it is activated and emitting ultrasound energy. Such movement of each of the double-faced transducer assemblies 38a, 38b, 38c, 38d is possible without having to move the handle element 100 or reposition the shaft 108, which simplifies the procedure for the surgeon and also minimizes patient discomfort during the procedure.

In the foregoing arrangement, during operation of the device 98, ultrasound energy is emitted by each double-faced transducer assembly 38a, 38b, 38c, 38d in a radially outward direction, with determinable focal zones (see, for example, FIGS. 2B and 2C). The method of operating the device 98 in accordance with the present invention, as well as the advantages achieved thereby, will be described in further detail hereinafter.

Like the device 66 of the first embodiment, the device 98 of second embodiment of the present invention may, in operation, be used in conjunction with a fluid-filled balloon, such as is well-known in the art for treating the endometrium (inner lining of the uterine cavity). Alternatively, the device 98 may be used without such a balloon and, instead the cavity or luminal structure should be filled with enough fluid to contact the tissue to be ablated and to submerge the double-faced transducer assemblies 38a, 38b, 38c, 38d positioned proximate to the tissue. The fluid is required to provide a medium for the ultrasound energy emitted from the ultrasound transducers to travel to, and be absorbed by, the tissues to be treated. For purposes of the following discussion, the cavity or luminal structure will be prepared for surgery and filled with a suitable fluid, such as saline, in a manner that is well-known to those of ordinary skill in the art and consistent with currently accepted medical/surgical standards.

Prior to activating one or more of the double-faced transducer assemblies 38a, 38b, 38c, 38d, the surgeon grips the handle element 100 of the device 98 and inserts the shaft 108, with the rods 122, 124, 126, 128 carried therein and the double-faced transducer assemblies 38a, 38b, 38c, 38d mounted thereon, into a cavity or luminal structure. The handle element 100 is moved, which, in turn, also moves the shaft 108, until the double-faced transducer assemblies 38a, 38b, 38c, 38d are proximate to at least a portion of the tissue in need of thermal ablation. The surgeon then turns the rotatable knob 116, which rotates the double-faced transducer assemblies 38a, 38b, 38c, 38d, as described hereinabove. The knob 116 is turned until the double-faced transducer assemblies 38a, 38b, 38c, 38d are oriented as desired by the surgeon, proximate to tissue and such that the tissue is located within the focal zones of one or more of the double-faced transducer assemblies 38a, 38b, 38c, 38d that will be activated. The RF power source (not shown) or sources are then turned on to activate one or more of the double-faced transducer assemblies 38a, 38b, 38c, 38d which then emit ultrasound energy that is, in turn, transmitted to the tissue, thereby heating the tissue.

After a clinically determined period of time, which will depend upon the nature and size of the tissue area being ablated and its distance from the double-faced transducer assemblies 38a, 38b, 38c, 38d, the knob 116 is again turned and the double-faced transducer assemblies 38a, 38b, 38c, 38d are thereby moved to another orientation relative to the handle element 100 and the shaft 108, such that additional tissue to be ablated is within the focal zone of one or more of the double-faced transducer assemblies 38a, 38b, 38c, 38d. Typically, the clinically determined period of time for which one or more of the double-faced transducer assemblies 38a, 38b, 38c, 38d remains activated proximate to a particular tissue area will be between about 1 and 5 minutes, but should be no more than about 10 minutes, and should preferably be from about 2 to 3 minutes. The double-faced transducer assemblies 38a, 38b, 38c, 38d are moved, in the foregoing manner, as many times as necessary to achieve the desired pattern of heating. After the desired pattern of heating is achieved, the RF power source is turned off. The desired pattern of heating will be determined by the surgeon, based upon clinical factors and experience, as discussed hereinabove in connection with the first embodiment of the present invention.

Of course, there are many possible variations and modifications to the present invention that are possible and would be readily understood by persons having ordinary skill in the art. For example, the energy-emitting surfaces (18, 44, 46, 48, 50) of the spool-shaped and double-faced transducer assemblies (10, 38) could be flat, rather than curved, whereby a collimated wave of ultrasound energy would be emitted therefrom. Moreover, each double-faced transducer assembly 38 may include only a first transducer element 40 (i.e., without any second transducer element 42), whereby each double-faced transducer assembly 38 would emit ultrasound energy only from the first surface 44 of the first transducer element 40. Similarly, each double-faced transducer assembly 38 may include only a second transducer element 42 (i.e., without any first transducer element 40), whereby each double-faced transducer assembly 38 would emit ultrasound energy only from the second surface 50 of the second transducer element 42.

In addition, the number of transducer assemblies mounted onto the devices 66, 98 of each embodiment may be varied. More particularly, one or more additional spool-shaped transducer assemblies, similar to the one described hereinabove (e.g., 10a), could be mounted, spaced apart axially from one another and the spool-shaped transducer assembly 10a already described, onto the shaft 78 and rod 90 of the device 66 of the first embodiment. With reference to the device 98 of the second embodiment, it could include as few as a single double-faced transducer assembly mounted onto a single rod, or it could include any number that can be reasonably sized and shaped so as to be positioned at the distal end 114 of the shaft 108 without interfering with the insertion of the shaft 108 and transducer assemblies into the patient's cavity or luminal structure. For example, the device 98 could include only two or three double-faced transducer assemblies mounted onto two or three rods, respectively. Alternatively, the device 98 could include five or six double-faced transducer assemblies mounted onto five or six rods, respectively, and positioned at the distal end 114 of the shaft 108 such that the transducers approximate the transverse cross-sectional size and shape of the shaft 108.

In addition to the foregoing configurations of double-faced transducer assemblies, it will be understood by those of ordinary skill in the art that the device 98 may include additional groups or rows of double-faced transducer assemblies movably mounted proximate to the first group of double-faced transducer assemblies 38a, 38b, 38c, 38d (not shown). Such a second group of transducers would extend axially from the first group of double-faced transducer assemblies 38a, 38b, 38c, 38d and from the distal end 114 of the shaft 108. More particularly, it will be recalled that each double-faced transducer assembly of a first group is mounted to a corresponding one of the rods 122, 124, 126, 128. In turn, each double-faced transducer assembly (not shown) of a second group would be mounted onto a corresponding one of the double-faced transducer assemblies of the first group. In the foregoing configuration, rotation of each of the double-faced transducer assemblies 38a, 38b, 38c, 38d of the first group would, in turn, cause concurrent, synchronous rotation of each of the double-faced transducer assemblies of the second group. Moreover, it is possible that additional groups (i.e., a third group, a fourth group, etc.) of double-faced transducer assemblies could be added to the device 98 by stacking them axially, as described above, onto the second group.

It is also possible that the rotatable knobs 74, 116 of the devices 66, 98 of the present invention may be moved by, or even entirely replaced by, a motor (such as an AC, DC or stepper motor), rather than being manually moved. Such a motor could be used to automatically move the rods 90, 122, 124, 126, 128 at a slow or fast rate, as determined by the surgeon.

Lastly, it is noted that, while the present invention enables movement of the transducer assemblies after insertion into the patient's body and while they are activated, without necessitating repositioning of the handle element and shaft, it is still, nonetheless, possible to reposition the transducer assemblies by moving the handle element and shaft after insertion into the patient's body and while the transducer assemblies are activated. Thus, the present invention expands the way in which the transducer assemblies can be repositioned within a patient's cavity or luminal structure, while not eliminating pre-existing ways of achieving such movement.

It will be understood that the embodiments described herein are merely exemplary and that a person skilled in the art may make many variations and modifications, including but not limited to those discussed hereinabove, without departing from the spirit and scope of the present invention. All such variations and modifications are intended to be included within the scope of the invention as defined in the appended claims.

What is claimed is:

1. A device for performing thermal ablation therapy, comprising
   a handle element sized and shaped to be held by a user;
   at least one transducer assembly which, when activated, emits ultrasound energy capable of heating tissue, said at least one transducer assembly being movably mounted relative to said handle element;
   moving means for moving said at least one transducer assembly, while activated, to any one of a plurality of positions relative to said handle element and relative to tissue to be ablated, whereby ultrasound energy is efficiently delivered to the tissue;
   a carrying element for carrying said moving means and said at least one transducer assembly, said carrying element being connected at one end to said handle element and having an opposite end located remote from said handle element, said carrying element and said moving means being sized and shaped for at least partial insertion into a patient's cavity or luminal structure; and
      actuating means for actuating said moving means, said actuating means engaging said moving means and being positioned proximate to said handle element such that said actuating means is manually accessible by a user, said actuating means including a rotatable knob.

2. The device according to claim 1, wherein said carrying means includes a shaft having a central longitudinal bore therethrough and a distal end located remote from said handle element.

3. The device according to claim 2, wherein said moving means includes at least one rod that is rotatably received within said bore, said at least one rod having a first end positioned proximate to said distal end of said shaft and a second end positioned proximate to said handle.

4. The device according to claim 3, wherein said distal end of said shaft engages said knob such that rotation of said knob results in rotation of said at least one rod and movement of said at least one transducer assembly.

5. The device according to claim 4, wherein said at least one rod includes external threads and said shaft includes a pair of diametrically opposed slots, each of which extends in a longitudinal direction relative to said shaft and communicates with said bore of said shaft.

6. The device according to claim 5, wherein said at least one transducer assembly includes a support nut for mounting said at least one transducer assembly on said at least one rod and on said shaft such that said at least one transducer assembly is longitudinally movable relative to said handle element and said shaft.

7. The device according to claim 6, wherein said support nut has a bore with internal threads and a pair of arcuate slots positioned on opposite sides of said bore, said support nut being sized and shaped such that, when said at least one transducer assembly is mounted on said rod and said shaft, said internal threads of said support nut are engaged with said external threads of said rod and portions of said shaft located intermediate said longitudinal slots are received within said arcuate slots of said support nut.

8. The device according to claim 7, wherein said at least one transducer assembly includes a spool-shaped transducer assembly having a support nut with a transducer element mounted thereon, said transducer element having an arcuate outer surface from which ultrasound energy is emitted in a controlled and focused manner.

9. The device according to claim 4, wherein said at least one rod includes a plurality of rods, said first end of each of said plurality of rods extending out of said distal end of said shaft.

10. The device according to claim 9, wherein said shaft includes a longitudinal axis and said knob includes a central toothed gear having an axis of rotatation, said knob being positioned such that said central toothed gear is positioned proximate to said shaft and axis of rotation of said central toothed gear is parallel to said longitudinal axis of said shaft.

11. The device according to claim 10, wherein said shaft has a lateral cross-sectional shape and said at least one transducer assembly includes a plurality of transducer assemblies, each of which is sized and shaped so that, when arrange proximate to one another, said plurality of transducer assemblies collectively have a shape that conforms at least approximately to said lateral cross-sectional shape of said shaft, thereby facilitating insertion of said shaft and said plurality of transducer assemblies into a patient's cavity or luminal structure.

12. The device according to claim 11, wherein each of said plurality of transducer assemblies has a rotational axis and is attached to said first end of a corresponding one of said plurality of rods such that said rotational axis of each of said plurality of transducer assemblies is parallel to said longitudinal axis of said shaft.

13. The device according to claim 12, wherein said moving means further includes a plurality of secondary toothed gear, each of which has a rotational axis and is connected to said proximal end of a corresponding one of said plurality of rods, said plurality of secondary toothed gears engaging said central toothed gear such that said rotational axis of each said plurality of secondary toothed gears is parallel to said longitudinal axis of said shaft and such that rotation of said central toothed gear causes substantially synchronous rotation of said secondary toothed gears, thereby causing rotation of each of said plurality of rods and hence, the rotation of each of said plurality of transducer assemblies.

14. The device according to claim 13, wherein each of said plurality of transducer assemblies has a first arcuate surface from which ultrasound energy is emitted in a first general direction in a controlled and focused manner and a second arcuate surface positioned opposite said first surface and from which ultrasound energy is emitted in a second general direction which is opposite said first general direction and in a controlled and focused manner.

15. The device according to claim 14, wherein said plurality of rods includes four rods, said plurality of transducer assemblies includes four transducer assemblies, and said plurality of secondary toothed gears includes four secondary toothed gears.

16. The device according to claim 15, wherein said lateral cross-sectional shape of said shaft is cylindrical.

* * * * *

UNITED STATES PATENT AND TRADEMARK OFFICE
CERTIFICATE OF CORRECTION

PATENT NO. : 7,004,940 B2 Page 1 of 1
APPLICATION NO. : 10/268448
DATED : February 28, 2006
INVENTOR(S) : Thomas P. Ryan and Gennady Kleyman It is certified that error appears in the above-identified patent and that said Letters Patent is hereby corrected as shown below:

col. 19, ln. 39, after "and" insert --said--;
col. 20, ln. 16, change "gear" to --gears--.

Signed and Sealed this

Fifteenth Day of August, 2006

JON W. DUDAS
*Director of the United States Patent and Trademark Office*